(12) United States Patent
Tanter et al.

(10) Patent No.: US 10,881,380 B2
(45) Date of Patent: Jan. 5, 2021

(54) METHOD FOR OBTAINING A FUNCTIONAL PARAMETER OF A MUSCLE

(71) Applicants: INSTITUT NATIONAL DE LA SANTE ET DE LA RECHERCHE MEDICALE (INSERM), Paris (FR); CENTRE NATIONAL DE LA RECHERCHE SCIENTIFIQUE (C.N.R.S.), Paris (FR); UNIVERSITÉ PIERRE ET MARIE CURIE (PARIS 6), Paris (FR); UNIVERSITÉ PARIS DIDEROT—PARIS 7, Paris (FR); ECOLE SUPERIEURE DE PHYSIQUE ET DE CHIMIE INDUSTRIELLES DE LA VILLE DE PARIS, Paris (FR)

(72) Inventors: Mickael Tanter, Paris (FR); Mathieu Pernot, Paris (FR)

(73) Assignees: INSTITUT NATIONAL DE LA SANTE ET DE LA RECHERCHE MEDICALE (INSERM), Paris (FR); CENTRE NATIONAL DE LA RECHERCHE SCIENTIFIQUE (C.N.R.S), Paris (FR); UNIVERSITE PIERRE ET MARIE CURIE (PARIS 6), Paris (FR); UNIVERSITE PARIS DIDEROT—PARIS 7, Paris (FR); ECOLE SUPERIEURE DE PHYSIQUE ET DE CHIMIE INDUSTRIELLES DE LA VILLE DE PARIS, Paris (FR)

( * ) Notice: Subject to any disclaimer, the term of this patent is extended or adjusted under 35 U.S.C. 154(b) by 609 days.

(21) Appl. No.: 15/325,103

(22) PCT Filed: Jul. 17, 2015

(86) PCT No.: PCT/EP2015/066440
§ 371 (c)(1),
(2) Date: Jan. 10, 2017

(87) PCT Pub. No.: WO2016/009057
PCT Pub. Date: Jan. 21, 2016

(65) Prior Publication Data
US 2017/0181729 A1 Jun. 29, 2017

(30) Foreign Application Priority Data
Jul. 17, 2014 (EP) .................................. 14306160

(51) Int. Cl.
*A61B 8/08* (2006.01)
*G01S 7/52* (2006.01)
*A61B 8/00* (2006.01)

(52) U.S. Cl.
CPC ............ *A61B 8/485* (2013.01); *A61B 8/0883* (2013.01); *A61B 8/461* (2013.01); *A61B 8/5207* (2013.01);
(Continued)

(58) Field of Classification Search
USPC ......................................................... 600/438
See application file for complete search history.

(56) References Cited

U.S. PATENT DOCUMENTS

| 2004/0059220 A1* | 3/2004 | Mourad | ............... A61B 5/0048 600/442 |
| 2007/0129639 A1* | 6/2007 | Zhang | .................. A61B 5/0452 600/509 |
| 2013/0211256 A1* | 8/2013 | Russell | .............. A61B 5/02028 600/438 |

FOREIGN PATENT DOCUMENTS

| CN | 1663534 A | 9/2005 |
| WO | 2004/002305 A2 | 1/2004 |
| WO | 2010/139519 A1 | 12/2010 |

OTHER PUBLICATIONS

Armen P Sarvazyan, Oleg V Rudenko, Scott D Swanson, J.Brian Fowlkes, Stanislav Y Emelianov. Shear wave elasticity imaging: a new ultrasonic technology of medical diagnostics,Ultrasound in Medicine & Biology, vol. 24, Issue 9, p. 1419-1435 (Year: 1998).*

*Primary Examiner* — Nathan J Jenness
(74) *Attorney, Agent, or Firm* — W&C IP

(57) ABSTRACT

The present invention concerns a method for obtaining a functional parameter of a muscle having a part, the method (Continued)

comprising the steps of: a) applying ultrasound waves to the muscle, b) collecting the ultrasound waves retrodiffused by the muscle at a plurality of times, to obtain collected ultrasound waves, c) determining a first plurality of values representative of stiffness values of one part at a first plurality of times by using the collected ultrasound waves, d) determining a second plurality of values representative of deformation values of said part at a second plurality of times by using the collected ultrasound waves, and e) deducing at least one functional parameter based on the first plurality of values and the second plurality of values. The invention also concerns a corresponding device.

16 Claims, 2 Drawing Sheets

(52) U.S. Cl.
CPC ...... *G01S 7/52022* (2013.01); *G01S 7/52042* (2013.01)

(56) References Cited

OTHER PUBLICATIONS

P. Wells et al., "Medical ultrasound: imaging of soft tissue strain and elasticity", Journal of the Royal Society Interface, Jun. 16, 2011, pp. 1521-1549, vol. 8.
M. Pernot et al., "Real-Time Assessment of Myocardial Contractility Using Shear Wave Imaging", Journal of the American College of Cardiology, Jun. 1, 2011, pp. 65-72, vol. 58, No. 1.
C. Pislaru et al., "Viscoelastic Properties of Normal and Infarcted Myocardium Measured by a Multifrequency Shear Wave Method: Comparison with Pressure-Segment Length Method", Ultrasound in Medicine & Biology, May 6, 2014, pp. 1785-1795, vol. 40, No. 8.
J. Gennisson et al., "Ultrasound elastography: Principles and techniques", Diagnostic and Interventional Imaging, May 1, 2013, pp. 487-495, vol. 94, No. 5.

\* cited by examiner

METHOD FOR OBTAINING A FUNCTIONAL PARAMETER OF A MUSCLE

TECHNICAL FIELD OF THE INVENTION

The invention relates to a method for obtaining at least one functional parameter of a muscle. The invention also concerns a method for monitoring the state of a muscle using such method for obtaining a functional parameter. The invention also relates to the associated device and system.

BACKGROUND OF THE INVENTION

The assessment of diastolic left ventricular function is critical for the evaluation of heart failure and ischemic cardiomyopathy. Myocardial stiffness is thought to play a key-role in diastolic function. For Heart Failure patients with preserved ejection fraction (labeled EF in the remainder of the specification), abnormalities in left ventricle (labeled LV in the remainder of the specification), relaxation and LV stiffness are one of the key pathophysiological mechanisms. Myocardial stiffness is also known to be a very strong prognosis parameter in hypertrophy and dilated cardiomyopathy.

In case of myocardial infarction, tissue Doppler and strain echocardiography are established methods to track myocardial deformation for the evaluation of the systolic function.

Shear wave elastography (SWE) is a more recent ultrasound technique that can measure quantitatively in real-time the shear modulus (i.e. stiffness) of soft tissues. SWE can quantify myocardial stiffness and its variation during the cardiac cycle.

However, the full characterization of the myocardium requires to measure at least two functional parameters such as myocardial stiffness and myocardial deformation.

SUMMARY OF THE INVENTION

The invention aims at enabling to provide a non-invasive characterization of myocardial function or muscular function.

To this end, the invention concerns a method for obtaining at least one functional parameter of a muscle having at least one part, the method comprising the steps of:

a) applying ultrasound waves to the muscle, b) collecting the ultrasound waves retrodiffused by the muscle at a plurality of times, to obtain collected ultrasound waves, characterized in that the method further comprises the steps of:

c) determining a first plurality of values representative of stiffness values of at least one part of the parts of the muscle at a first plurality of times by using the collected ultrasound waves, the first plurality of times being included in the plurality of times, d) determining a second plurality of values representative of deformation values of said part at a second plurality of times by using the collected ultrasound waves, the second plurality of times being included in the plurality of times and being associated with the first plurality of times in a one-to-one relationship, and e) deducing at least one functional parameter based on the first plurality of values and the second plurality of values.

Thanks to the invention, the diastolic myocardial stiffness is accessible in a non-invasive way.

Such access is notably enabled by the two distinct steps c) and d) wherein, in a simultaneous way, the values representative of stiffness values and the values representative of deformation values are respectively obtained by a sequence of measurements carried out on the muscle. Each measurement is achieved by using the collected ultrasound waves.

Such approach enables to avoid the estimation of stress-strain relationship. Stress cannot be measured non-invasively and requires a linear approximation (Hooke's law) to be derived from strain measurements only. Such Hooke's law is an approximation in the case of biological tissues and even more in the case of a muscle. In other words, by avoiding the use of the Hooke's law, the variation observed between the linear relationship and the real relationship gives access to the functional parameter of the muscle.

As such variation is obtained in a non-invasive way by only using ultrasound waves, the method for obtaining at least one functional parameter of the muscle is a non-invasive method.

According to further aspects of the invention which are advantageous but not compulsory, the method for obtaining at least one functional parameter might incorporate one or several of the following features, taken in any technically admissible combination:

- steps a) and b) are carried out in vivo.
- the muscle has a cycle having a temporal duration, the absolute value of the difference between a time of the first plurality of times and the associated time of the second plurality of times below or equal to 200 milliseconds modulo the temporal duration of the cycle of the muscle.
- the functional parameter is representative of the mechanical work of the part, the first plurality of values and the second plurality of values forming a stiffness-deformation loop and at step e), the functional parameter is the area of the stiffness-deformation loop.
- the first plurality of values and the second plurality of values form a stiffness-deformation loop with four inflexion points and step e) comprises determining, for at least one of the inflexion point, a first value representative of stiffness value and a second value representative of deformation value.
- the first plurality of values and the second plurality of values form a stiffness-deformation loop with four inflexion points linked by four parts and step e) comprises curve fitting at least one of the part by an exponential function whose coefficient is the functional parameter.
- the muscle has reflecting particles and at step a), at least one focused ultrasound wave is applied to generate an elastic shear wave in the muscle and a succession of ultrasound waves are applied so that at least some of said ultrasound waves penetrate into an area of the muscle while the shear wave is propagating in the same area and at step b), the collected ultrasound waves are echoes generated by the ultrasound compression waves interacting with reflecting particles in the muscle.
- the method further comprises a step of storing the at least one deduced functional parameter in a memory unit.
- the method further comprises a step of displaying the at least one deduced functional parameter on a display unit.
- the muscle is the myocardium, the part is at least a segment of the myocardium and the functional parameter is at least one of end-diastolic passive myocardial stiffness, myocardium work, the passive myocardial stiffness variation with deformation and the end-systolic myocardial stiffness.

steps a) to e) are iterated to obtain a plurality of values for the functional parameter.

each iteration of steps a) to e) corresponds to different operating conditions for the muscle.

It is also proposed a method for monitoring the state of a muscle comprising the step of carrying out the method for obtaining at least one functional parameter of said muscle as previously described, to obtain a plurality of values for at least one functional parameter of said muscle. The method for monitoring the state of a muscle also comprises a step of comparing the plurality of values for the functional parameter with a plurality of expected values for the functional parameter according to a comparison criterion, and a step of emitting a warning in case the comparison criterion is not met.

According to a preferred embodiment, the muscle is the myocardium and the state is chosen in the group consisting of in good health, in stunning state, in ischemia and in infarction.

It also concerns a device for obtaining at least one functional parameter of a muscle having at least one part, the device comprising an applying unit adapted to apply ultrasound waves to the muscle and a collecting unit adapted to collect the ultrasound waves retrodiffused by the muscle at a plurality of times, to obtain collected ultrasound waves. The device also comprises a calculator being adapted to carry out the step of determining a first plurality of values representative of stiffness values of at least one part of the parts of the muscle at a first plurality of times by using the collected ultrasound waves, the first plurality of times being included in the plurality of times. The calculator is further adapted to determine a second plurality of values representative of deformation values of said part at a second plurality of times by using the collected ultrasound waves, the second plurality of times being included in the plurality of times and being associated with the first plurality of times in a one-to-one relationship. The calculator is also adapted to deduce at least one functional parameter based on the first plurality of values and the second plurality of values.

It is also proposed a system for monitoring the state of a muscle comprising a device for obtaining at least one functional parameter of a muscle as previously described, the device being adapted to obtain a plurality of values for at least one functional parameter of said muscle. The system also comprises a comparator adapted to compare the plurality of values for the functional parameter with a plurality of expected values for the functional parameter according to a comparison criterion, and a warning unit adapted to emit a warning in case the comparison criterion is not met.

BRIEF DESCRIPTION OF THE DRAWINGS

The invention will be better understood on the basis of the following description which is given in correspondence with the annexed figures and as an illustrative example, without restricting the object of the invention. In the annexed figures.

DETAILED DESCRIPTION OF SOME EMBODIMENTS

Figure 1:
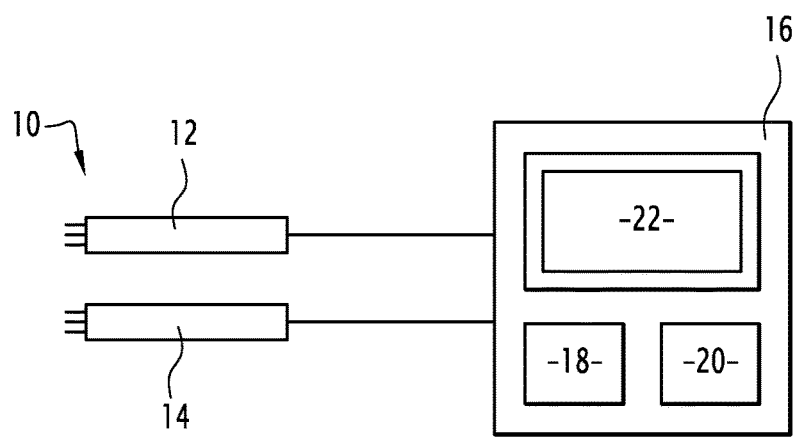
FIG. 1 is a schematic representation of a device for obtaining at least one myocardial functional parameter.

A device 10 for obtaining at least one myocardial functional parameter is represented on FIG. 1.

Such device 10 is adapted to obtain a myocardial functional parameter. By definition, a functional parameter is a parameter relative to the properties of the muscle, a parameter relative to the metabolism of the muscle or a parameter relative to the operation of the muscle.

A myocardial functional parameter is, for instance, the end-diastolic passive myocardial stiffness, myocardium work of a specific segment of the myocardium, the passive myocardial stiffness variation with deformation or the end-systolic myocardial stiffness.

The device 10 comprises an applying unit 12, a collecting unit 14 and a computer unit 16.

The applying unit 12 is adapted to apply ultrasound waves to the myocardium.

According to the example of FIG. 1, the applying unit 12 comprises an array of transducers.

Alternatively, the applying unit 12 comprises only one transducer.

The collecting unit 14 is adapted to collect the ultrasound waves retrodiffused by the muscle.

According to the example of FIG. 1, the collecting unit 14 comprises an array of transducers.

Alternatively, the collecting unit 14 comprises only one transducer.

According to another embodiment, the applying unit 12 and the collecting unit 14 are the same unit.

The computer unit 16 comprises a calculator 18, a memory unit 20 and a displaying unit 22.

The calculator 18 is adapted to carry out calculation.

According to the example of FIG. 1, the calculator 18 is a processor.

The memory unit 20 is adapted to store data.

The displaying unit 22 is adapted to display data.

For instance, the displaying unit 22 is a screen.

According to another embodiment, the calculator 18, the memory unit 20 and the displaying unit 22 are comprised in a watch. This enables to obtain a portable device 10.

Operation of the device 10 is now described in reference to a method for obtaining at least one myocardial functional parameter.

The applying unit 12 applies one focused ultrasound wave to the myocardium by using the applying unit 12. The focused ultrasound wave generates an elastic shear wave in the muscle.

The applying unit 12 then applies a succession of ultrasound waves so that at least some of said ultrasound waves penetrate into a segment of the myocardium while the shear wave is propagating in the same segment of the myocardium.

As the myocardium has reflecting particles, echoes are generated by the ultrasound compression waves interacting with reflecting particles in the myocardium. Such echoes are called retrodiffused ultrasound waves.

In a specific embodiment, the succession of ultrasound waves is a succession of focused ultrasound waves. This is notably the case for ultrafast imaging.

In another embodiment, the succession of ultrasound waves is a succession of unfocused ultrasound waves. This is notably the case for cardioscope.

The collecting unit 14 then collects the retrodiffused ultrasound waves at a plurality of times.

Such collection enables to obtain a plurality of images which can be analyzed to determine values.

The calculator 18 then determines a first plurality of values representative of stiffness values of at least one part of the parts of the muscle at a first plurality of times by using the collected ultrasound waves, the first plurality of times being included in the plurality of times.

A value is representative of stiffness is any physical quantity linked to the stiffness.

For instance, the shear modulus μ of the myocardium is a value representative of stiffness. As shear waves propagate in a muscle in an anisotropic way, such shear modulus μ is a mean value of several shear modulus $\mu_{direction}$ of the myocardium along several directions.

Alternatively, the shear modulus $\mu_{direction}$ of the myocardium in a specific direction is also a value representative of stiffness. The shear modulus which is along the direction of the fibers of the myocardium labeled $\mu_{parallel}$ and the shear modulus which is along the direction perpendicular to the direction of the fibers of the myocardium labeled $\mu_{perpendicular}$ are examples of shear modulus of the myocardium in a specific direction.

As another example, the Young's modulus E of the myocardium is a value representative of stiffness. By definition, the Young's modulus E is linked to the shear modulus μ by the relation E=3μ. As shear waves propagate in a muscle in an anisotropic way, such Young's modulus μ is a mean value of several Young's modulus $E_{direction}$ of the myocardium along several directions.

Alternatively, the Young's modulus $E_{direction}$ of the myocardium in a specific direction is also a value representative of stiffness. The Young's modulus which is along the direction of the fibers of the myocardium labeled $E_{parallel}$ and the Young's modulus which is along the direction perpendicular to the direction of the fibers of the myocardium labeled $E_{perpendicular}$ are examples of Young's modulus of the myocardium in a specific direction.

As another example, the propagation speed $c_S$ of shear waves in the myocardium is a value representative of stiffness. The propagation speed $c_S$ of shear waves in the myocardium is linked to the Young's modulus $E_{direction}$ by the following relation:

$$c_s = \sqrt{\frac{E}{3\rho}} \quad [1]$$

wherein ρ is the density of the myocardium.

As shear waves propagate in a muscle in an anisotropic way, such propagation speed $c_S$ of shear waves in the myocardium is a mean value of several propagation speeds $c_{S\_direction}$ of shear waves in the myocardium along several directions.

Alternatively, the propagation speed $c_{S\_direction}$ of shear waves in the myocardium in a specific direction is also a value representative of stiffness. The propagation speed of shear waves along the direction of the fibers in the myocardium labeled $c_{S\_parallel}$ and the propagation speed of shear waves along the direction perpendicular to the direction of the fibers in the myocardium labeled $c_{S\_perpendicular}$ are examples of propagation speed $c_{S\_direction}$ of shear waves in the myocardium in a specific direction.

The calculator 18 then determines a second plurality of values representative of deformation values of said part at a second plurality of times by using the collected ultrasound waves.

A value is representative of deformation is any physical quantity linked to the deformation.

The cumulative deformation is an example of value representative of deformation.

The length of the segment is an example of value representative of deformation.

Such length is measured along any direction. The length along the direction of the fibers, the length along the direction perpendicular to the direction of the fibers are specific examples of length of the segment which may be considered.

The length of the segment which is normalized to a reference length is another example of value representative of deformation.

The volume of the ventricle is also representative of the deformation.

The second plurality of times is included in the plurality of times and is associated with the first plurality of times in a one-to-one relationship.

Preferably, the absolute value of the difference between a time of the first plurality of times and the associated time of the second plurality of times below or equal to 100 milliseconds modulo the temporal duration of the cardiac cycle.

In case the measurement are carried out during the same cardiac cycle, the absolute value of the difference between a time of the first plurality of times and the associated time of the second plurality of times below or equal to 200 milliseconds.

More preferably, the absolute value of the difference between a time of the first plurality of times and the associated time of the second plurality of times below or equal to 20 milliseconds modulo the temporal duration of the cardiac cycle.

In case the measurement are carried out during the same cardiac cycle, the absolute value of the difference between a time of the first plurality of times and the associated time of the second plurality of times below or equal to 20 milliseconds.

Figure 3:
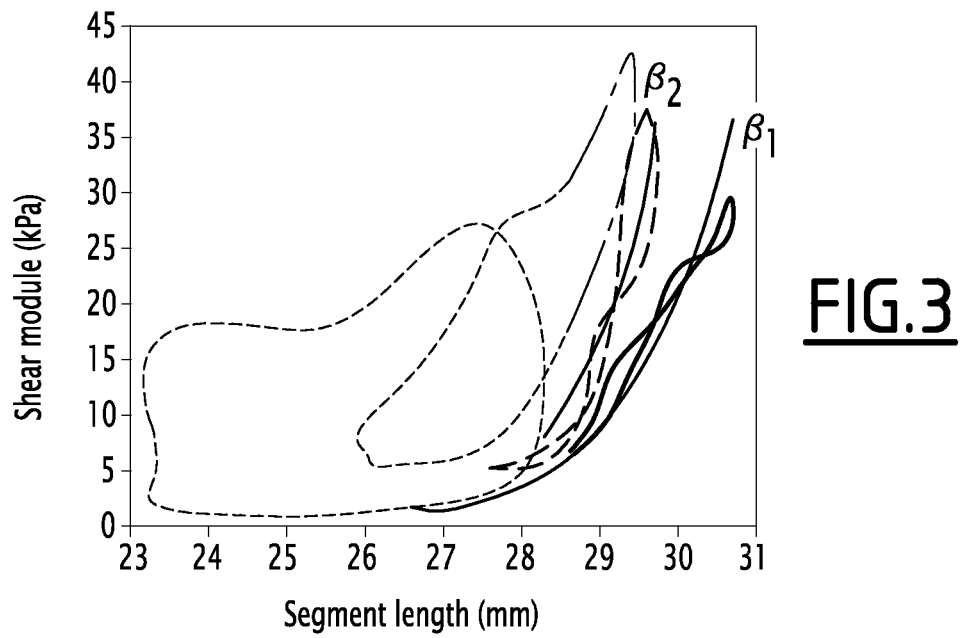
FIG. 3 is graph illustrating examples of stiffness-segment loops.

As visible on FIG. 3, the first plurality of values and the second plurality of values form a stiffness-deformation loop. FIG. 3 illustrates examples of stiffness-segment loops. Stiffness measured by SWE is plotted as a function of segment length for baseline (in dotted line), 5 minutes after coronary occlusion (in full line), 2 hours after occlusion (in thick line), and 40 minutes after reperfusion (in dot-dash line).

Such loop comprises four inflexion points linked by four parts, a lower part, an upper part and lateral parts. When the loop is followed continuously starting from the lower part, the lower part is followed, then the first lateral part is followed, then the upper part is followed and then the second lateral part is followed.

In the specific case of myocardium, the inflexion point which is common to the lower part and the first lateral part is called end diastolic point whereas the inflexion point which is common to the upper part and the second lateral part is called end systolic point.

The calculator 18 then deduces at least one myocardium functional parameter based on the first plurality of values and the second plurality of values.

Figure 4:
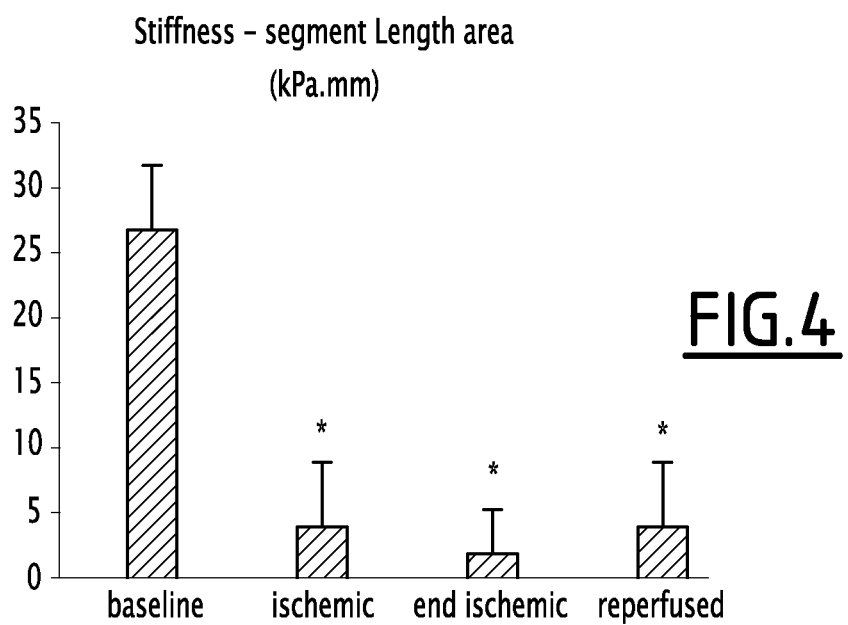
FIG. 4 is a graph showing the evolution of mechanical work of the studied myocardial segment based on FIG. 3.

According to an example, the myocardium functional parameter is representative of the mechanical work of the segment. In such case, the myocardium functional parameter is obtained by calculating the area of the stiffness-deformation loop. Such calculation is illustrated schematically on FIG. 4 given the data of FIG. 3.

According to another example, at the step of deducing, at least one part is curve fitted by an exponential function whose coefficient is the myocardium functional parameter.

For instance, the myocardium functional parameter is representative of the end diastolic passive myocardial stiffness and such myocardium functional parameter is obtained by curve-fitting the lower part. FIG. 3 illustrates such step of curve-fitting by showing two exemplary exponential functions which fits the lower part of two loops. These two exemplary exponential functions has respectively two coefficients labeled β1 and β2.

According to another example, the step of deducing comprises determining, for at least one of the inflexion point, a first value representative of stiffness value (stiffness coordinate) and a second value representative of deformation value (deformation coordinate).

For instance, in the case of myocardium, it is valuable to obtain the stiffness coordinates and the deformation coordinates of the end-diastolic point and of the end-systolic point.

At the end of the deducing step, at least one myocardial functional parameter is deduced.

Such deduced myocardial functional parameter is stored in the memory unit 20 and displayed on the displaying unit 22.

The method for obtaining at least one myocardial functional parameter enables to obtain a myocardial functional parameter by using a stiffness-deformation loop.

Such stiffness-deformation loop is obtainable in a non-invasive way. Indeed, according to a preferred embodiment, the measurements implied in the method for obtaining are carried out in vivo.

In addition, the method for obtaining at least one myocardial functional parameter enables to access to myocardial functional parameters which are not easily accessible to the methods belonging to the prior art. Notably, the mechanical work of the segment of the myocardium is a quantity which is difficult to access for the methods of the prior art.

Furthermore, it can be shown that the method for obtaining at least one myocardial functional parameter is as accurate as invasive methods.

Such accuracy has been demonstrated experimentally. Indeed, experiments using the device 10 were performed on an open chest ovine model. After sternotomy, the ultrasonic transducer of the applying unit 12 was placed in front of the left ventricular free wall. A sequence combining shear wave imaging and strain imaging was used. Shear wave imaging was performed at a repetition rate of 15 Hz during 1 s to quantify the myocardial stiffness change over a cardiac cycle. Myocardial strain was measured on the ultrasound images during the same cardiac cycles. The stiffness-strain curve loop was obtained from these two non-invasive ultrasound based measurements. The same experiment was performed during coronary occlusion on the ischemic wall. The area of the loop was strongly reduced (almost equal to 0) compared to baseline. The area of stiffness-strain loop correlated with the work of the segment.

Such method for obtaining a functional parameter is also applicable for other muscle. For instance, the muscle is uterus or a muscle involved in the practicing of a sport.

According to an embodiment, such method for obtaining a functional parameter is iterated several times to obtain a plurality of values for the myocardial functional parameter.

In such cases, comparisons are achievable.

The comparison may be carried out for different operating conditions for the myocardium. For instance, the myocardium may be subjected to drug or the person may be in a different stage of physical effort.

The comparison may also be temporal such that an evolution of the functional parameter may indicate an abnormality of operating of the myocardium.

Figure 2:
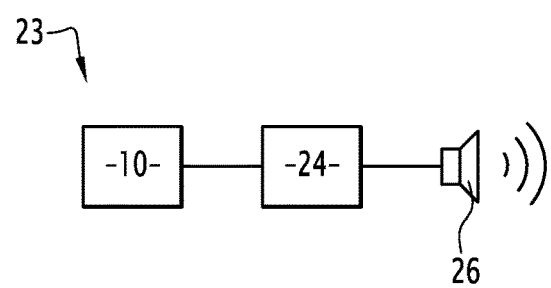
FIG. 2 is a schematic representation of a system for monitoring the state of myocardium, the system comprising the device of FIG. 1.

For this, as represented on FIG. 2, it is proposed a system 23 for monitoring the state of the myocardium. By the expression "state", it is meant an evaluation of the operating of the myocardium. Ill and healthy are states of myocardium. Intermediate state exists. For instance, a heart murmur is also a state of myocardium.

The system 23 comprises the device 10 for obtaining at least myocardium as illustrated on FIG. 1, a comparator 24 and a warning unit 26.

The device 10 is adapted to a plurality of values for at least one myocardial functional parameter of the myocardium.

The comparator 24 is adapted to compare the plurality of values for the myocardial functional parameter with a plurality of expected values for the myocardial functional parameter according to a comparison criterion.

The comparator 24 is, for instance, a processor.

The comparison criterion may differ according to the kind of monitoring.

As an example, the comparison criterion is a predetermined threshold. For instance, if the mechanical work of a segment is below a given value, this means the considered segment is not in the healthy state.

As an example, the comparison criterion is relative to the evolution of the myocardial functional parameter with time and notably, the value of the derivative of the myocardial functional parameter with time at given time.

For preventing infarction, a comparison criterion related to the end-diastolic passive myocardial stiffness has shown a strong correlation between the end-diastolic passive myocardial stiffness and the infarction.

For detecting ischemia, a comparison criterion related to an evolution of the mechanical work of a segment is considered The warning unit 26 is adapted to emit a warning in case the comparison criterion is not met.

The warning may be an audible alarm or a visible alarm.

Such system 23 enables to monitor efficiently the state of the myocardium.

Preferably, the system 23 is portable.

The embodiments and alternative embodiments considered here-above can be combined to generate further embodiments of the invention.

The invention claimed is:

1. Method for obtaining at least one functional parameter of a muscle having at least one part, the method comprising the steps of:
   a) applying ultrasound waves to the muscle,
   b) collecting the ultrasound waves retrodiffused by the muscle at a plurality of times, to obtain collected ultrasound waves,
   c) determining a first plurality of values representative of stiffness values of at least one part of the parts of the muscle at a first plurality of times by using the collected ultrasound waves, the first plurality of times being included in the plurality of times, each value representative of stiffness is selected from the group consisting of a shear modulus of the muscle, a Young's modulus of the muscle, and a propagation speed of shear waves in the muscle,
   d) determining a second plurality of values representative of deformation values of said part at a second plurality of times by using the collected ultrasound waves, the second plurality of times being included in the plurality of times and being associated with the first plurality of times in a one-to-one relationship, each value representative of deformation is selected from the group consisting of a cumulative deformation, a length of the muscle, a normalized length of the muscle and a volume of the muscle, and e) deducing at least one functional parameter based on the first plurality of values and the second plurality of values, wherein the first plurality of values and the second plurality of values form a stiffness-deformation loop.

2. Method for obtaining at least one functional parameter according to claim 1, wherein steps a) and b) are carried out in vivo.

3. Method for obtaining at least one functional parameter according to claim 1, wherein the muscle has a cycle having a temporal duration, the absolute value of the difference between a time of the first plurality of times and the associated time of the second plurality of times below or equal to 200 milliseconds.

4. Method for obtaining at least one functional parameter according to claim 1, wherein the functional parameter is representative of the mechanical work of the part, and wherein at step f), the functional parameter is the area of the stiffness-deformation loop.

5. Method for obtaining at least one functional parameter according to claim 1, wherein the first plurality of values and the second plurality of values form a stiffness-deformation loop with four inflexion points and wherein step f) comprises determining, for at least one of the inflexion points, a first value representative of stiffness value and a second value representative of deformation value.

6. Method for obtaining at least one functional parameter according to claim 1, wherein the first plurality of values and the second plurality of values form a stiffness-deformation loop with four inflexion points linked by four parts and wherein step f) comprises curve fitting at least one of the parts by an exponential function whose coefficient is the functional parameter.

7. Method for obtaining at least one functional parameter according to claim 1, wherein the muscle has reflecting particles, wherein at step a), at least one focused ultrasound wave is applied to generate an elastic shear wave in the muscle and a succession of ultrasound waves are applied so that at least some of said ultrasound waves penetrate into an area of the muscle while the shear wave is propagating in the same area and wherein at step b), the collected ultrasound waves are echoes generated by ultrasound compression waves interacting with reflecting particles in the muscle.

8. Method for obtaining at least one functional parameter according to claim 1, wherein the method further comprises a step of storing the at least one deduced functional parameter in a memory unit.

9. Method for obtaining at least one functional parameter according to claim 1, wherein the method further comprises a step of displaying the at least one deduced functional parameter on a displaying unit.

10. Method for obtaining at least one functional parameter according to claim 1, wherein the muscle is the myocardium, the part is at least a segment of the myocardium and the functional parameter is at least one of end-diastolic passive myocardial stiffness, myocardium work, the passive myocardial stiffness variation with deformation and the end-systolic myocardial stiffness.

11. Method for obtaining at least one functional parameter according to claim 1, wherein steps a) to f) are iterated to obtain a plurality of values for the functional parameter.

12. Method for obtaining at least one functional parameter according to claim 1, wherein several iterations of steps a) to f) are carried out and each iteration corresponds to different operating conditions for the muscle.

13. Method for monitoring a state of a muscle comprising the steps of:
carrying out the method for obtaining at least one functional parameter of said muscle according to claim 11, to obtain a plurality of values for at least one functional parameter of said muscle,
comparing the plurality of values for the functional parameter with a plurality of expected values for the functional parameter according to a comparison criteria, and
emitting a warning in case the comparison criteria is not met.

14. Method according to claim 13, wherein the muscle is the myocardium and the state is chosen in the group consisting of in good health, in stunning state, in ischemia and in infarction.

15. Device for obtaining at least one functional parameter of a muscle having at least one part, the device comprising:
an applying unit adapted to apply ultrasound waves to the muscle,
a collecting unit adapted to collect the ultrasound waves retrodiffused by the muscle at a plurality of times, to obtain collected ultrasound waves,
a calculator being adapted to carry out the steps of:
determining a first plurality of values representative of stiffness values of at least one part of the parts of the muscle at a first plurality of times by using the collected ultrasound waves, the first plurality of times being included in the plurality of times, each value representative of stiffness is selected from the group consisting of a shear modulus of the muscle, a Young's modulus of the muscle, and a propagation speed of shear waves in the muscle,
determining a second plurality of values representative of deformation values of said part at a second plurality of times by using the collected ultrasound waves, the second plurality of times being included in the plurality of times and being associated with the first plurality of times in a one-to-one relationship, each value representative of deformation is selected from the group consisting of a cumulative deformation, a length of the muscle, a normalized length of the muscle and a volume of the muscle, and
deducing at least one functional parameter based on the first plurality of values and the second plurality of values, wherein the first plurality of values and the second plurality of values form a stiffness-deformation loop.

16. System for monitoring the state of a muscle comprising:
a device for obtaining at least one functional parameter of a muscle according to claim 15, the device being adapted to obtain a plurality of values for at least one functional parameter of said muscle,
a comparator adapted to compare the plurality of values for the functional parameter with a plurality of expected values for the functional parameter according to a comparison criterion, and
a warning unit adapted to emit a warning in case the comparison criterion is not met.

* * * * *